United States Patent [19]

Désérable et al.

[11] Patent Number: 5,674,508
[45] Date of Patent: Oct. 7, 1997

[54] COSMETIC COMPOSITION FOR COMPOSING STICKS FOR THE LIPS OR THE SKIN AND PROCESSES FOR THE PREPARATION THEREOF

[75] Inventors: Véronique Désérable, Paris; Jean Claude Bernard, Creteil, both of France

[73] Assignee: Laboratoires de Biologie Vegetale Yves Rocher, La Gacilly, France

[21] Appl. No.: 487,848

[22] Filed: Jun. 7, 1995

[30] Foreign Application Priority Data

Jul. 15, 1994 [FR] France .................................. 94 08813

[51] Int. Cl.⁶ .................................................. A61K 7/025
[52] U.S. Cl. ............................................ 424/401; 424/64
[58] Field of Search ............................. 424/401, 64

[56] References Cited

U.S. PATENT DOCUMENTS 4,960,764  10/1990  Figueroa et al. .................. 514/939

FOREIGN PATENT DOCUMENTS 0 374 332   6/1990   European Pat. Off. .
0 456 459  11/1991   European Pat. Off. .
2 050 163   1/1981   United Kingdom .

OTHER PUBLICATIONS

Fodor et al., Derwent Abstract of EP612517, 1994.

Primary Examiner—Thurman K. Page
Assistant Examiner—Sharon Howard
Attorney, Agent, or Firm—Young & Thompson

[57] ABSTRACT

The subject of the invention is a cosmetic composition for composing sticks for the lips or the skin comprising an anhydrous base in which is dispersed an emulsion of water-in-silicone type, the said emulsion consisting of an aqueous phase dispersed in a lipophilic phase comprising one or more silicones.

15 Claims, No Drawings

COSMETIC COMPOSITION FOR COMPOSING STICKS FOR THE LIPS OR THE SKIN AND PROCESSES FOR THE PREPARATION THEREOF

The present invention relates to a new cosmetic composition for composing sticks for the lips or the skin, to a process for its preparation and to the sticks for the lips and the skin as such.

The sticks for the lips or the skin disclosed in the prior art generally consist of a mixture of various anhydrous and/or lipophilic constituents such as waxes (natural, vegetable, mineral or synthetic), oils (vegetable or mineral) and other fatty substances (liquid fatty esters, synthetic triglycerides and solid fatty esters).

In order to make possible uniform application on the skin, to avoid any granular consistency in the formulation and to provide for its stability on storage, many compositions have been developed by determining the nature and the respective proportions of the constituents which have to be combined.

The preparation of coloured sticks for the lips is one of the cosmetics industry's major preoccupations. It especially requires the use of colouring materials.

Until now, the use of water-soluble dyes was, however, limited insofar as poor distribution of the water-soluble dyes in the lipophilic base was generally observed, due to the hydrophilic properties of these constituents.

For this reason, the water-soluble dyes are introduced in very small amounts into the lipstick compositions of the state of the art.

As an alternative, the use of pigments such as iron, chromium or manganese oxides, ultramarines, organic lakes, natural dyes or mother-of-pearl has been advocated. These are ground beforehand in a fatty binder before being added to the mixture. The use of these pigments, however, poses the problem of their poor incorporation in the mixture due to imperfect impregnation of the lipophilic base on the particles, which leads to a granular appearance of the resulting composition. In order to overcome this disadvantage, the use of complex processes, carried out under vacuum for example, has been proposed.

The compositions of the state of the art do not generally make it possible to incorporate effective amounts of water-soluble substances. Now, the addition of such substances is of great advantage from the cosmetological viewpoint. In addition to the dyes already cited, mention will be made, as hydrophilic substances, of moisturizers, softening products, emollients, soothing and restructuring products, astringents, refreshing products, nourishing products and trace elements.

The present invention is targeted at providing sticks for the lips or the skin which can contain a significant proportion of such hydrophilic substances.

The compositions of the invention are moreover characterized by a particularly pleasant texture, conferring a soft, smooth and glossy appearance on the skin. The spreading of the compositions on the skin is easy and the non-greasy feel which they provide is very noticeable.

These properties of the sticks for the lips and the skin of the invention result from their specific formulation.

More precisely, the first subject of the invention is a cosmetic composition for composing sticks for the lips or the skin comprising an anhydrous base in which a water-in-silicone emulsion is dispersed.

The anhydrous base is composed of the constituents commonly used in cosmetics, such as the waxes, oils or fatty substances defined above. It can also comprise other additives such as preservatives, fragrances or indeed even pigments.

The water-in-silicone emulsion consists of an aqueous phase dispersed in a lipophilic phase comprising one or more silicones.

According to the invention, silicone is understood to mean organosilylated polymers comprising Si—O—Si bonds. This definition comprises a large number of silicones which are known in the art and marketed, such as: cetyl dimethicones, cyclomethicones, dimethicones, dimethicone copolyols, dimethicone copolyol acetates, $C_1$–$C_5$ alkyl ethers of dimethicone copolyol-PG-betaines, dimethicone silylates, copolymers of dimethicone/sodium thiosulphate ad of PG-propyldimethicone, dimethiconols, methicones, phenethyl disiloxanes, stearoxy dimethicones, phenyl dimethicones, dimethicone/stearoxy methicone copolymers and stearoxytrimethylsilanes.

Dow Coming (USA), Goldschmidt (Germany), Rhône-Poulenc (France), Union Carbide (USA) and Bayer (Germany) may be mentioned as manufacturers of silicones.

These various silicones have been denoted according to the nomenclature of the C.T.F.A. (Cosmetic, Toiletry and Fragrance Association) dictionary.

A preferred group of silicones consists of polydimethylsiloxanes, polydimethylsiloxanes modified by ionic and non-ionic organic groups and methylphenylpolysiloxanes.

Mention will particularly be made, as polydimethylsiloxanes, of the dimethicones of formula:

$$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-CH_3$$

where n is an integer of less than 5,000, and the cyclomethicones of formula:

$$-\left[\underset{\underset{CH_3}{|}}{\overset{\overset{CH_3}{|}}{Si}}-O\right]_n-$$

where n is an integer of less than 10.

Likewise, polydimethylsiloxanes modified by non-ionic groups include the dimethicone copolyols, which are dimethyl siloxane polymers having side chains of polyoxyethylene and/or polyoxypropylene type, the stearoxy dimethicones, which are dimethyl polysiloxane polymers containing end stearoxy groups at their extremities, and the stearyl dimethicones.

Finally, as preferred methylphenylpolysiloxanes, mention will more particularly be made of the phenyl dimethicones of formula $$H_3C-\left[\underset{\underset{C_6H_5}{|}}{\overset{\overset{CH_3}{|}}{Si}}-O\right]_n-\underset{\underset{C_6H_5}{|}}{\overset{\overset{CH_3}{|}}{Si}}-CH_3$$

where n is an integer of less than 5,000.

The physicochemical properties of the silicones which can be used according to the invention and especially their hydrophobicity, their thermalstability, their solubility in organic media, their viscosity, their emulsifying properties and their substantivity vary according to their linear, branched or cyclic structure, the nature of the functional groups which they contain and their molecular mass.

By way of example, the dimethicones which can be used according to the invention have a kinematic viscosity of between $1.10^{-2}$ m²/s and $6.10^{-2}$ m²/s, their surface tension being approximately $2.10^{-2}$ N/m.

Likewise, the cyclomethicones preferably used have a surface tension of approximately $17.10^{-3}$ N/m.

Moreover, the emulsifying properties of a large number of modified polydimethylsiloxanes will be pointed out. Dimethicone polyols are especially known for their emulsifying properties.

It is especially by varying these property differences of the silicones that a person skilled in the art can modify the physicochemical properties of the resulting emulsion, by selecting the appropriate combinations of silicones.

Preferably, the whole of the silicones contained in the composition of the invention represent from 1 to 50% by weight of the emulsion, better still from 5 to 30% or alternatively from 10 to 25%.

In addition to the silicone constituents, the lipophilic phase of the emulsion can comprise an ester such as the ester of an acid and of a linear or branched $C_1$–$C_3$ alcohol.

The ester contributes to improving the cohesion of the composition of the invention by its excellent compatibility with the silicones of the emulsion, on the one hand, and with the various constituents of the anhydrous base, on the other hand.

2-Ethylhexyl laurate is particularly indicated as ester, insofar as it is very well tolerated by the skin.

As a general rule, the ratio by mass of the ester to the whole of the silicones is between 1:3 and 2:1.

The lipophilic phase can contain other types of additives, such as antioxidants, liposoluble dyes, fragrances or liposoluble sunscreening agents.

A person skilled in the art knows that it is possible to use, as antioxidants, sorbic acid, citric acid, ascorbyl palmitate, butylated hydroxyanisole (BHA) end butylated hydroxytoluene (BHT), and vitamin E and its derivatives.

However, the content of additives in the lipophilic phase of the emulsion will not exceed 10% by weight and preferably 5%.

The aqueous phase of the compositions of the invention makes it possible to incorporate many water-soluble substances having varied activities. Depending on the desired aim, it is possible to envisage the addition to the aqueous phase of moisturizers, such as urea, sodium hyaluronate, sodium pyrrolidonecarboxylate (sodium PCA) or sodium lactate, softening products, such as D-panthenol, emollients, such as polyethylene glycol, humectants, such as glycereol, propylene glycol, sorbitol or butylene glycol, soothing and restructuring products, such as allantoin, astringents, such as alcloxa, UV-protection products, such as 2-phenylbenzimidazole-5-sulphonic acid, refreshing products, such as menthol, nourishing products, such as acacia honey or water-soluble vitamins, trace elements or synthetic water-soluble dyes, such as Blue No. 1, Yellow No. 5, Red No. 4 or Green No. 3, or natural water-soluble dyes, such as beetroot, caramel, chlorophyll or curcumin.

The water content of the emulsion is preferably between 30 and 90% by weight and better still between 50 and 80% by weight.

It is the dispersion of the water-in-silicone emulsion in the anhydrous base of the compositions of the invention which confers on the latter their particularly pleasant consistency and provides the non-greasy feel which is highly sought after in cosmetics.

In a preferred embodiment, the water-in-silicone emulsion used according to the invention represents 0.5 to 50% by weight of the cosmetic composition of the invention and better still from 10 to 40% by weight.

In order to produce the emulsion and to ensure its stability, it is necessary to introduce an emulsifying agent therein. Such agents are known in the art.

Although the actual nature of the emulsifying agent is not essential according to the invention, it is preferable to choose a silicone with emulsifying properties, such as a modified polydimethylsiloxane and for example a dimethicone copolyol.

Moreover, so as to control the viscosity and the consistency of the resulting water-in-silicone emulsion, it may be useful to incorporate a gelling agent therein.

The gelling agents which can be used in the invention are those generally used in cosmetics. Mention may be made, as examples of such gelling agents, of modified bentones, xanthan gums, carboxymethyl cellulose, galactomannans, crosslinked polyacrylic acids, silica, gelatin, alginates and pectins, as well as agar gel.

Many other types of ingredients can be added to the emulsion, such as preservatives or fragrances.

The invention also relates to a process for the preparation of the compositions of the invention.

This process comprises the steps consisting of a) maintaining, under stirring, a lipophilic phase comprising especially one or more silicones at a temperature of between room temperature and 100° C. until the mixture is completely homogenized, b) simultaneously preparing a homogeneous aqueous phase comprising water, optionally with one or more water-soluble substances added, c) incorporating, with stirring, the aqueous phase prepared in step b) in the lipophilic phase prepared in step a), d) if appropriate, cooling the resulting emulsion to room temperature, e) dispersing the said emulsion in an appropriate anhydrous base so as to compose a stick for the lips or the skin.

In order to homogenize the aqueous solution of the emulsion, it is possible to heat it by bringing, for example, the solution to a temperature of between room temperature and 90° C.

When antioxidants or esters are added to the emulsion, the latter are incorporated in the lipophilic phase before step c). An emulsifying agent is also introduced at the same time.

When a gelling agent is used, the latter can be either added to the emulsion following the incorporation of the aqueous phase into the lipophilic phase or dispersed in one of these phases or alternatively in both phases.

Moreover, it is desirable that the optional additives of the emulsion, such as preservatives or fragrances, are only added during the cooling of the emulsion, that is to say during step d), due to their possible thermal instability.

Finally, according to a preferred embodiment, the water-soluble dyes used are incorporated in the emulsion during step d), optionally mixed with fragrances or preservatives, essentially for the purpose of preventing them from being degraded by the heat.

The compositions of the invention can be provided in the form of sticks for the lips or the skin.

Mention may be made, as examples of sticks for the lips or the skin which come within the context of the invention, of lipsticks, stick deodorants and sticks for the hands, chest and feet.

The shaping of the sticks for the lips or the skin is carried out conventionally.

The composition of the invention is poured in the molten state into moulds provided for this purpose. The moulds are filled to the brim so as to prevent the formation of a depression at the centre of the moulds. After cooling and removing from the moulds, the sticks of the invention are obtained.

The following examples are given solely by way of illustration of the present invention and should in no way be regarded as limiting the scope of the latter.

EXAMPLE 1

Example 1 illustrates more precisely the preparation of various water-in-silicone emulsions.

In the proposed formulations, the lipophilic phase of the invention, marked as A, contains, in addition to the silicones, 2-ethylhexyl laurate as ester and sorbic acid as antioxident.

In the aqueous phase of the emulsion, marked as B, several typical water-soluble substances have been incorporated.

The use of modified bentone, carboxymethyl cellulose, silica and gelatin as gelling agent (phase C) has, moreover, been illustrated. Finally, the composition of Formulation (c) exemplifies the incorporation of water-soluble dyes.

The preparation process comprises the following steps consisting in:

- heating, with stirring, the elements of A at the temperature necessary for the complete homogenization of the mixture,
- preparing a homogeneous aqueous solution of the constituents of B by bringing it, if necessary, to a temperature of between room temperature and 90° C.,
- incorporating, with stirring, the aqueous phase B in the lipophilic phase A,
- dispersing, in the resulting emulsion, phase C which has been homogenized beforehand or which has been dispersed beforehand in a part of the appropriate phase and which comprises the whole of the gelling agents used,
- bringing the mixture to 25° C.,
- then incorporating phase D, homogenized beforehand, comprising the fragrances, preservatives and, if appropriate, the water-soluble dyes.

In the following formulations, the percentages indicated are percentages by weight.

Formulation (a)

| phase A | Dimethicone copolyol | 4.0 to 6.0 |
|---|---|---|
| phase A | Sorbic acid | 0.2 to 0.5 |
| phase A | 2-Ethylhexyl laurate | 5.0 to 15.0 |
| phase A | Dimethicone copolymer | 3.0 to 6.0 |
| phase A | Polysiloxane | 5.0 to 10.0 |
| phase B | Water | q.s. for 100 |
| phase B | Sodium hyaluronate | 0.1 to 0.5 |
| phase B | Propylene glycol | 5.0 to 10.0 |
| phase C | Modified bentone | 1.5 to 3.0 |
| phase D | Preservatives | 0.5 to 1.0 |
| phase D | Fragrance | 0.1 to 0.3 |

The polysiloxane can be a polydimethylsiloxane or a polyphenylmethylsiloxane.

Formulation (b)

| phase A | Dimethicone copolyol | 4.0 to 6.0 |
|---|---|---|
| phase A | Sorbic acid | 0.2 to 0.5 |
| phase A | 2-Ethylhexyl laurate | 5.0 to 15.0 |
| phase A | Phenyl dimethicone | 3.0 to 6.0 |
| phase A | Cyclomethicone | 4.0 to 6.0 |
| phase B | Water | q.s. for 100 |
| phase B | Sodium hyaluronate | 0.1 to 0.5 |
| phase B | Propylene glycol | 5.0 to 10.0 |
| phase B | Urea | 1.0 to 5.0 |
| phase B | Sorbitol | 1.0 to 5.0 |
| phase C | Carboxymethyl cellulose | 0.5 to 1.5 |
| phase D | Preservatives | 0.5 to 1.0 |
| phase D | Fragrance | 0.1 to 0.3 |

Formulation (c)

| phase A | Dimethicone copolyol | 4.0 to 6.0 |
|---|---|---|
| phase A | Sorbic acid | 0.2 to 0.5 |
| phase A | 2-Ethylhexyl laurate | 5.0 to 15.0 |
| phase A | Stearoxy dimethicone | 1.0 to 2.5 |
| phase A | Dimethylpolysiloxane | 3.0 to 6.0 |
| phase B | Water | q.s. for 100 |
| phase B | Sodium hyaluronate | 0.1 to 0.5 |
| phase B | Propylene glycol | 5.0 to 10.0 |
| phase C | Gelatin | 0.5 to 2.0 |
| phase C | Silica | 0.4 to 1.0 |
| phase D | Water-soluble dye | 0.05 to 0.2 |
| phase D | Preservatives | 0.5 to 1.0 |
| phase D | Fragrance | 0.1 to 0.3 |

It should be noted that, in each case, the proportion of water added is the amount of water necessary to bring the weight of the composition to 100%.

EXAMPLE 2

The preparation of a stick for the lips or the skin based on a water-in-silicone emulsion is illustrated in Example 2.

The various constituents of the prepared stick are the following (in % by weight):

| phase A | Beeswax | 2 to 6 |
|---|---|---|
| | Carnauba wax | 1 to 4 |
| | Lanolin | 1 to 5 |
| | Mineral oils | 5 to 10 |
| | Antioxidant | 0.05 to 0.20 |
| phase B | Pigments | 0.5 to 10 |
| | Triglycerides | q.s. for 100 |
| phase C | Water-in-silicone emulsion | 10 to 40 |

The water-in-silicone emulsion used can be any one of the emulsions (a), (b) or (c) described in Example 1.

In a first step, the constituents of phase A are mixed in the molten state at a temperature of between 70° and 90 ° C.

At the same time, the pigments are ground in the fatty binder of phase B.

Phase B is then incorporated in phase A with stirring. Phase C is then added to the mixture which has been kept stirring.

Once homogenization has been obtained, the resulting paste is poured into a mould provided for this purpose. Removal of the stick from the mould takes place at room temperature.

We claim:

1. Cosmetic composition for composing sticks for the lips or the skin comprising an anhydrous base in which a water-in-silicone emulsion is dispersed, the said emulsion consisting of an aqueous phase dispersed in a lipophilic phase comprising one or more silicones.

2. Composition according to claim 1, characterized in that the said silicone(s) represent(s) from 1 to 50% by weight of the emulsion.

3. Composition according to claim 1, characterized in that the said silicone(s) is/are chosen from cetyl dimethicones, cyclomethicones, dimethicones, dimethicone copolyols, dimethicone copolyol acetates, $C_1$–$C_5$ alkyl ethers of dimethicone copolyol-PG-betaines, dimethicone silylates, copolymers of dimethicone/sodium thiosulphate and of PG-propyldimethicone, dimethiconols, methicones, phenethyl disiloxanes, stearoxy dimethicones, phenyl dimethicones, dimethicone/stearoxy methicone copolymers and stearoxytrimethylsilanes.

4. Composition according to claim 1, characterized in that the said silicone(s) is/are selected from polydimethylsiloxanes, and especially dimethicones and cyclomethicones, polydimethylsiloxanes modified by ionic or non-ionic organic groups, and especially dimethicone copolyols, stearyl dimethicones or stearoxy dimethicones, and methylphenylpolysiloxanes, especially phenyl dimethicones.

5. Composition according to claim 1, characterized in that the lipophilic phase of the emulsion additionally contains an ester, such as the ester of an acid and of a linear branched $C_1$–$C_{30}$ alcohol.

6. Composition according to claim 1, characterized in that the aqueous phase of the emulsion comprises water-soluble substances such as moisturizers, softening products, emollients, humectants, soothing and restructuring products, astringents, refreshing products, nourishing products, trace elements, water-soluble dyes or water-soluble sunscreening agents.

7. Composition according to claim 1, characterized in that the emulsion comprises an emulsifying agent.

8. Composition according to claim 7, characterized in that the emulsifying agent is a silicone with emulsifying properties and especially a modified polydimethylsiloxane such as a dimethicone copolyol.

9. Composition according to claim 1, characterized in that the emulsion additionally comprises a gelling agent, such as a modified bentone, a xanthan gum, carboxymethyl cellulose, a galactomannan, a crosslinked polyacrylic acid, silica, gelatin, an alginate, a pectin or agar gel.

10. Process for the preparation of a composition for composing sticks for the lips or the skin comprising an anhydrous base in which a water-in-silicon emulsion is dispersed, the said emulsion consisting of an aqueous phase dispersed in a lipophilic phase comprising one or more silicones, characterized in that it comprises the steps consisting of:

a) maintaining, under stirring, a lipophilic phase comprising especially one or more silicones at a temperature of between room temperature and 100° C. until the mixture is completely homogenized, b) simultaneously preparing a homogeneous aqueous phase comprising water, optionally with one or more water-soluble substances added, c) incorporating, with stirring, the aqueous phase prepared in step b) in the lipophilic phase prepared in step a), d) if appropriate, cooling the resulting emulsion to room temperature, e) dispersing the said emulsion in an appropriate anhydrous base so as to compose a stick for the lips or the skin.

11. Process according to claim 10, characterized in that a gelling agent is incorporated in the emulsion prepared in step c) or else the said gelling agent is dispersed in a part of the aqueous phase or in a part of the lipophilic phase or alternatively in both.

12. Process according to claim 10, characterized in that, when the composition comprises water-soluble dyes, the latter are added to the emulsion during step d).

13. Composition according to claim 1, in the form of a stick for the lips or the skin.

14. Cosmetic composition according to claim 1, wherein said composition is a solid at room temperature.

15. Process according to claim 10, wherein step (e) is performed with said anhydrous base in a molten state at elevated temperature, and further comprises cooling the resulting said composition to room temperature, in order to solidify said composition.

* * * * *